United States Patent [19]
Terry, Jr. et al.

[11] Patent Number: 5,707,400
[45] Date of Patent: Jan. 13, 1998

[54] TREATING REFRACTORY HYPERTENSION BY NERVE STIMULATION

[75] Inventors: Reese S. Terry, Jr.; Ross G. Baker, Jr., both of Houston, Tex.; Andre Marquette, Stamford, Conn.

[73] Assignee: Cyberonics, Inc., Webster, Tex.

[21] Appl. No.: 531,175

[22] Filed: Sep. 19, 1995

[51] Int. Cl.⁶ ..................................................... A61N 1/18
[52] U.S. Cl. ................................................................ 607/44
[58] Field of Search ........................................ 607/44, 45

[56] References Cited

U.S. PATENT DOCUMENTS

| | | | |
|---|---|---|---|
| 3,650,277 | 3/1972 | Sjostrand et al. | 607/44 |
| 5,199,428 | 4/1993 | Obel et al. | 128/703 |
| 5,299,569 | 4/1994 | Wernicke et al. | 607/45 |

*Primary Examiner*—Scott Getzow
*Attorney, Agent, or Firm*—Wigman, Cohen, Leitner & Myers, P.C.

[57] ABSTRACT

A method of treating patients suffering from refractory hypertension includes identifying a patient suffering from the disorder and applying a stimulating electrical signal to the patient's vagus nerve predetermined to modulate the electrical activity of the nerve and to alleviate the hypertension. The step of applying the stimulation may be performed manually by the patient, or automatically following detection of the hypertension by sensing the patient's blood pressure, or, preferably by continuous or periodic application without use of a sensor. The stimulating signal is a pulse waveform with programmable signal parameter values including pulse width, output current, frequency, on time and off time.

10 Claims, 4 Drawing Sheets

TREATING REFRACTORY HYPERTENSION BY NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient. More particularly, the invention resides in techniques for treating patients suffering from hypertension, by application of such signals to the vagus nerve or other cranial nerve, using an implanted neurostimulating device. Specifically, the invention is directed toward treating high blood pressure by selective modulation of the patient's vagus nerve activity.

Hypertension, or elevated blood pressure, is a relatively common affliction. A 1993 Canadian study of 1,374 individuals ranging from 30 to 69 years of age found that 32% of the male adults and 19% of the female adults in the study exhibited high blood pressure. Most patients with hypertension exhibit the hemodynamic abnormality of increased vascular resistance. Treatment is essential to limit secondary organ damage to the heart, kidneys and eyes, and other effects which tend to contribute to early death of the hypertensive person.

Refractory hypertension is characterized by blood pressure that remains above 140/90 mm Hg (160/90 mm Hg where the subject is greater than 60 years of age) despite treatment with at least two anti-hypertensive drugs for a period of time that is normally adequate to relieve the symptoms. The cause of the refractory hypertension is the basis on which the disorder is classified. Some examples are secondary hypertension, where a specific underlying disorder—such as kidney disease—is present; presence of exogenous substances which may increase blood pressure or interfere with anti-hypertensive medication; biological factors—such as obesity; inappropriate or inadequate treatment of the disorder; and noncomplying drug ingestion attributable to complex dosing schedules or medicinal side effects.

The current treatment of choice of physicians for patients suffering from refractory hypertension is a regimen of anti-hypertensive drugs, along with adoption by the patient of appropriate dietary changes and a regular schedule of exercise. The regimen is aimed at decreasing the systemic vascular resistance by interfering with the sympathetic nervous system. Commonly prescribed classes of pharmaceuticals include diuretics, adrenergic blockers, angiotensin converting enzyme (ACE) inhibitors, vasodilators, and calcium channel blockers (e.g., A. Neusy et al, *Refractory Hypertension: Definition, Prevalence, Pathophysiology, and Management, Seminars in Nephrology,* Vol. 10, No. 6, November 1990, pp. 546–51). It has been suggested that successful treatment may be attainable in 90% of the cases by means of a two-drug regimen (J. F. Setaro et al, *Refractory Hypertension, The New England Journal of Medicine,* Vol. 327, No. 8, pp.543–47). Nevertheless, many studies have reported a persistence of refractory hypertension in up to about 18% of the patient population studied, despite use of such a regimen (J. F. Setaro et al, Ibid.).

Moreover, as is typical with patients taking prescribed drugs over a period of time, various undesirable side effects can tend to produce other problems, such as loss of sex drive, drowsiness, restlessness, or anxiety.

A principal aim of the present invention is to provide a new and improved therapy for treating refractory hypertension disorders which is not only safe and effective but avoids the undesirable side effects that have characterized known treatments such as drug therapy.

According to the invention, refractory hypertension disorders are treated and controlled using vagus nerve stimulation to selectively and controllably modulate the nerve's electrical activity in a predetermined manner to alleviate the disorder.

Another broad object of the invention is to provide a therapy for treating refractory hypertension which does not require scheduled actions by the patient.

SUMMARY OF THE INVENTION

The vagus nerve provides autonomic innervation of the aortic arch baroceptors with acute reflexes to acute changes in blood pressure. It also provides autonomic innervation of both the atrioventricular node and the sinoatrial node, each of which slows the heart rate. The aortic baroreceptors may be manipulated to modulate blood pressure, with signals from the arch of the aorta transmitted through the vagus nerve into the tractus solitarus in the medullary area of the brain stem.

A further aim of the present invention is to provide a new and improved therapy for treating refractory hypertension by modulating the electrical activity of the vagus nerve in a manner to prevent elevation of the patient's blood pressure or to reduce the blood pressure. Such treatment is believed to act as a neuromodulator, which lowers the blood pressure through neurotransmitters.

In a preferred embodiment and method of the invention for treating hypertension, a neurostimulator which includes a stimulus generator is implanted in the patient to generate an electrical output signal, preferably configured as a sequence of pulses in which the electrical and timing parameters have programmable values. These parameter values are selected by the attending physician to be within ranges predetermined to be appropriate for the treatment. The properly configured pulse signal is applied to the patient's vagus nerve through an electrode set of a lead implanted on the nerve at a preselected site, preferably in the patient's neck.

The nerve stimulation is designed to modulate the electrical activity of the nerve and release neurotransmitters, serving as a neuromodulator to control the patient's blood pressure. Neurotransmitters are classified as either excitatory or inhibitory. While modulating signals may be selected to stimulate or inhibit, for purposes of this disclosure both functions are sometimes included within the term "stimulating" (and its variations) in this specification.

The specific stimulating signal pattern used to achieve a desired effect of the vagal modulation for a prescribed treatment is selected based on various factors, including the individual patient, specific nature of the hypertension disorder, and nerve fibers to be activated. The stimulation strategy also depends on factors such as whether a symptom or indicator of the disorder can be sensed to activate the neurostimulator, or a physiologic parameter can be detected to trigger the stimulation, and whether a refractory period after the stimulation interval allows the benefits of the nerve activity modulation to persist.

The basic treatment and control system of the device comprises a neurostimulator including signal generator, sensors, and leads. Also included are external electronics for calibration, programming, and periodic adjustment of parameters by the attending physician according to the needs of the particular patient, and for monitoring the implanted device operation, through telemetry. Preferably, the implanted electronics package (programmable stimulus generator) is implemented or programmed to be activated prophylactically, either for continuing stimulation, with regular intervals of interruption that may be linked to the patient's circadian cycle, or for sustained periodic stimulation. Alternatively, the device may be automatically triggered to deliver the prescribed therapy in response to sensing predetermined levels of elevated blood pressure of the patient, or manually triggered by the patient for a sustained period of stimulation at specified times, such as during periods of particular physical stress, for example.

BRIEF DESCRIPTION OF THE DRAWINGS

The above and still further objects and attendant advantages of the present invention will be better understood from a consideration of the ensuing detailed description of a currently contemplated best mode of practicing the invention, including presently preferred embodiments and methods thereof, taken in conjunction with the accompanying drawings, in which.

DESCRIPTION OF THE PRESENTLY PREFERRED EMBODIMENT AND METHOD

A generally suitable form of neurostimulator for use in the present invention is disclosed in U.S. Pat. No. 5,154,172 of R. Terry, Jr., et al. (referred to herein as "the '172 patent"), assigned to the same assignee as the instant application. The specification of the '172 patent is incorporated herein in its entirety by reference, but for the sake of convenience to the reader, certain portions are summarized in this application, together with modifications and additions to be described.

Figure 1:
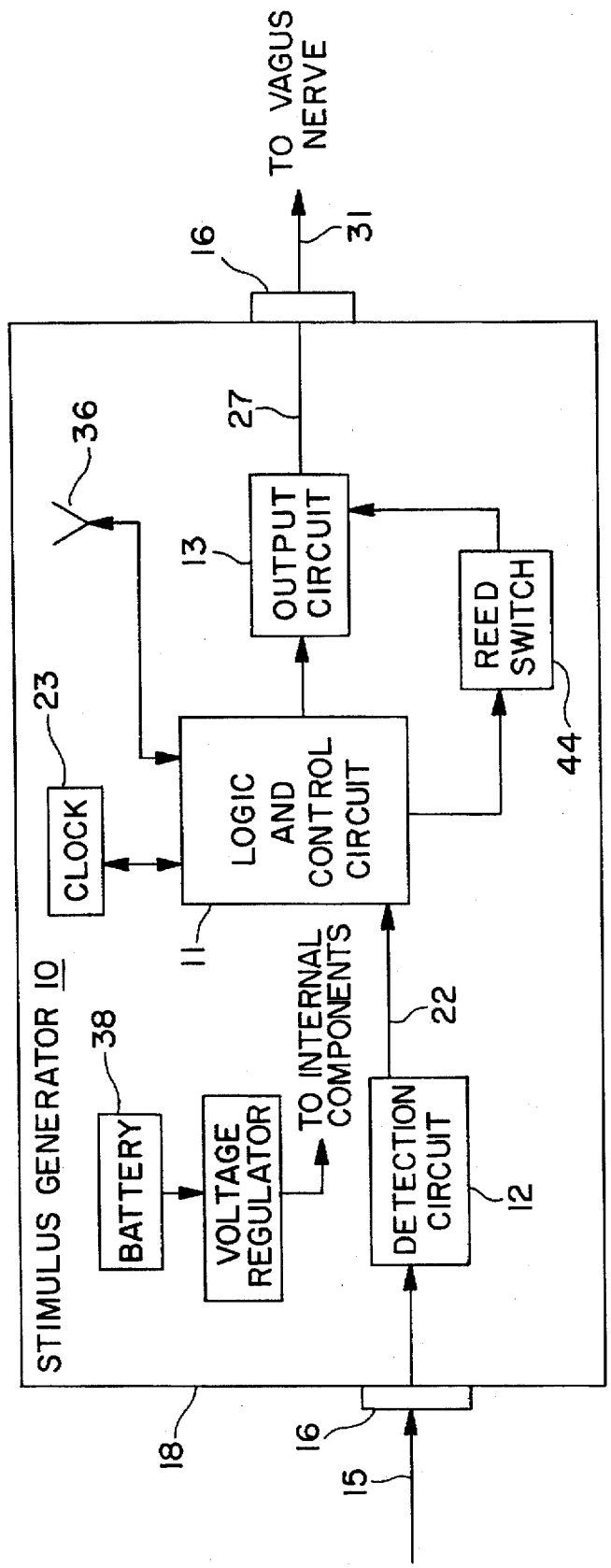
FIG. 1 is a simplified block diagram of a stimulus generator of the overall neurostimulator adapted to be implanted in the patient and programmed with appropriate parameter settings and ranges for treating refractory hypertension according to the present invention.
Figure 2:
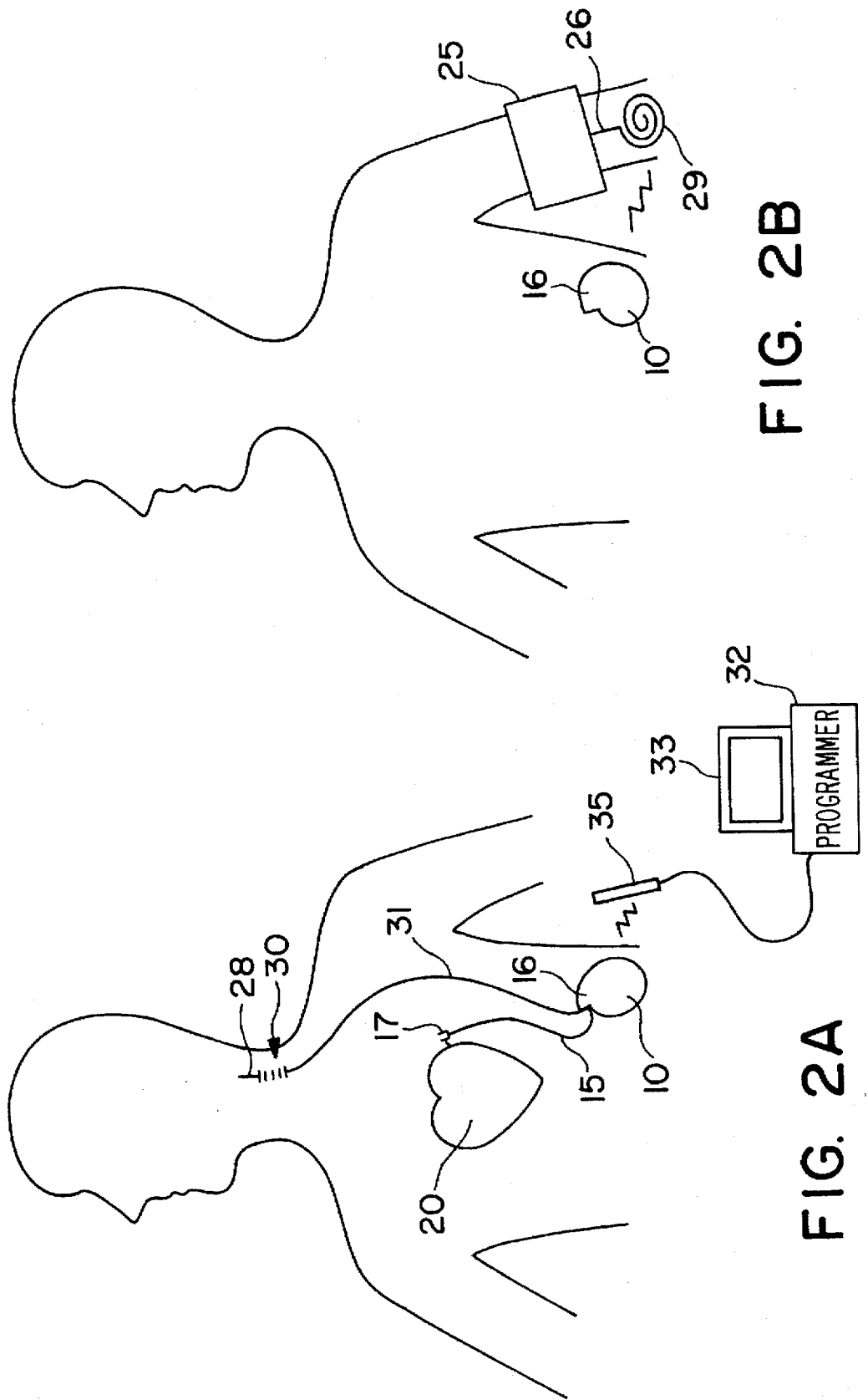
FIGS. 2A and 2B are simplified fragmentary illustrations of the stimulus generator and lead/electrode systems of the neurostimulator implanted in the patient's body, showing alternative embodiments of blood pressure sensors for a sensor-triggered version of the neurostimulator.

Referring to the drawings, FIG. 1 is a simplified block diagram of the stimulus generator 10 containing the electronics of the implantable neurostimulator. The neurostimulator is microprocessor-based and communicates with an external programmer by asynchronous serial communication to permit control or monitoring of states of the device. The stimulus generator is implanted in the patient's body, preferably in a pocket formed just below the skin in the abdomen (FIG. 2) during implant surgery.

In conjunction with its microprocessor-based logic and control circuit 11, the stimulus generator includes detection circuitry 12 (such as a sense amplifier that receives an input signal from a separate blood pressure sensor located externally or at an appropriate implant site) for automatically initiating the generation of a stimulating electrical signal by the generator. An output circuit 13 of the generator configures or patterns the stimulating signal according to programming of the device by the attending physician from an external programmer, to modulate the natural electrical activity of the vagus nerve in a manner to treat and control the patient's refractory hypertension.

The detection circuit 12 is coupled to the proximal end of a separately implantable lead 15 via a connector 16 mounted on the case 18 that houses the generator. The lead 15 itself is of conventional structure, including internal elongate conductors covered with an insulation layer or sheath which is biocompatible with the tissue and fluids of the body. At the distal end of the lead, the conductors are electrically connected to a set of electrodes 17 (FIG. 2A). The case 18 is composed of a metal which is biocompatible with the body's tissue and fluids, such as titanium.

Electrodes 17 preferably constitute a quadripolar array in which associated ones of two pairs are secured to preselected sites; for example, on opposite sides of and adjacent to an artery in relatively close proximity to the heart 20 to sense injected signal variations attributable to small electrical resistance changes associated with the periodic blood pressure variations occurring with the patient's heart beat. The electrodes may be composed of activated iridium, rhodium, or platinum, for example, and preferably are coated with a thin surface layer of iridium oxide to enhance electrical sensitivity. Each electrode may be provided with a biocompatible fabric "collar" or band about the electrode periphery to allow it to be readily sutured in place.

A quadripolar array will permit the two pairs of electrodes to be secured adjacent the selected artery so that a low level electrical signal generated by a small signal generator which may be incorporated in the detection circuit and applied across one pair can be detected across the other pair. The detection pair output is fed back to the detection circuit via lead 15. Changes in relative amplitude of the detected signal are proportional to changes in electrical resistance or impedance of the signal path as blood is pumped from the patient's heart through the selected artery. As the artery undergoes periodic alternate expansion and contraction with the heart rate in the region between the sensing electrodes, the resistance in both the signal and sensing paths alternately decreases and increases, respectively.

These impedance changes cause alternately lower and higher amplitudes in the detected signal, from which systolic and diastolic blood pressure can be determined by logic in detection circuit 12. The detection circuit thereby produces a digital output signal on conductive path 22 which is representative of the patient's blood pressure, for application to logic and control circuit 11.

When the detected systolic or diastolic level of blood pressure exceeds a respective predetermined threshold value as determined by circuit 11, that circuit triggers and configures the stimulating output signal of output circuit 13. In this sensor-triggered embodiment, the stimulating signal is delivered for a prescribed interval of time deemed sufficient to reduce the elevated blood pressure of the particular patient to an acceptably lower level, and is then terminated.

Instead of using a sensor implanted in the form of electrodes sutured adjacent a selected artery, the device may employ a conventional arm cuff sensor 25 (FIG. 2B) or finger cuff sensor (not shown), modified to generate an electrical signal indicative of the patient's blood pressure through an electrically conductive lead 26 and a telemetry coil 29. The latter coil transmits the pressure data through the patient's skin to the implanted generator, which will respond as programmed. Here, as in the previous embodiment, continuous detection of blood pressure by circuit 11 automatically triggers vagus nerve stimulation by device 10 when blood pressure sporadically increases above a predetermined threshold level. Operation then proceeds in the same manner as the internal sensor-triggered embodiment described above.

The preferred method of treating and controlling the patient's hypertension, however, uses the device's internal clock 23 having a crystal oscillator to provide timing signals for device operation, and which is additionally programmable from an external programmer unit 32 (FIG. 2A). The clock 23 is set from the external programmer to selectively trigger one or the other of continuous or periodic applications of the stimulating electrical signal to the patient's vagus nerve. That is, the stimulation program may be ongoing without interruption, or it may be repeated periodically for a preset interval of time, unless and until it is changed through programming by the attending physician. Another alternative using the internal clock is to set the timing of delivery of stimuli according to a regular pattern based on the patient's circadian rhythm.

When activated by logic and control circuit 11, output circuit 13 produces a pulsed signal having the desired electrical and timing parameters that have been programmed by the attending physician. The output circuit is connected via an internal conductive path 27 to additional receptacles of connector 16. In FIG. 1, connector 16 is shown at two different locations, but it will be understood that this depiction is merely for the sake of simplicity in illustrating inputs and outputs of the device. A single connector 16, with an appropriate number of receptacles, is mounted on or integral with the case 18 to accommodate all of the electrical connections to and from internal circuitry of the stimulus generator to receptacles in the connector.

A nerve stimulation electrode set 30 at the distal end of another lead 31 is implanted on the patient's vagus nerve 28 (FIG. 2A, and in greater detail in FIG. 3), and the proximal end of this lead is inserted into the proper receptacle(s) of connector 16 for conductive connection to the output signal path 27 of the generator 10.

The portion of the system external to the patient's body is intended for use by the attending physician to program the implanted device and to monitor its performance. This external portion includes a programing wand 35 which communicates with the implanted device by means of telemetry via an internal antenna 36 to transmit parameter values (as may be selectively changed from time to time by subsequent programing) selected at the programmer unit 32. The programming wand also accepts telemetry data from the stimulus generator to monitor the performance of the implanted device.

This portion of the system is completely conventional in that it may be substantially the same as is used for programming and monitoring various other types of implantable medical devices, with structure and operation well understood by persons skilled in the art. The programmer unit may be implemented as an IBM-compatible personal computer with associated monitor 33 and software for performing the functions described above in conjunction with communication between the implanted electronics and the programmer unit (FIG. 2A). The programming software of the type copyrighted by the assignee of the instant application with the Register of Copyrights, Library of Congress, or other suitable software based on the description herein.

The stimulus generator is powered by a battery or battery pack 38 of conventional type such as one or more lithium thionyl chloride cells, having a pair of output terminals electrically connected to the input terminals of a voltage regulator 40. The smooth regulated output voltage may be enhanced by voltage multiplication or division if desired, to power logic and control circuit 11 as well as other electronic components of the implantable device. Programmable parameters of the output signal of the device are controlled by circuit 11. These include current or voltage, frequency, pulse width, on-time, off-time, and start delay time. As a result, the output signal can be configured, selectively, before being applied to lead 31 and via the lead conductors to the electrodes 30 for stimulating the vagus nerve. Tailoring of the signal parameters to the patient's needs produces the desired modulation of the electrical activity of the vagus nerve for treatment and control of the refractive hypertension.

As an alternative to automatic stimulation, whether of the ongoing, or periodic, or sensor-triggered type, a reed switch 44 may be incorporated as part of generator 10 to allow the patient to manually activate the implanted device by placing an external magnet (not shown) in close proximity to the device, adjacent the skin, when symptoms or signs indicative of hypertension are apparent from the patient's own senses. Various other types of suitable manual activating means are disclosed in U.S. Pat. No. 5,304,206 of R. Baker, Jr. et al., issued Apr. 19, 1994, which is assigned to the assignee of this application. As with the sensor-triggered embodiment, the stimulating signal is delivered to the vagus nerve for a predetermined time interval deemed sufficient to reduce the particular patient's blood pressure to an acceptably lower level, and is then terminated.

In operation of the implanted device, upon detection of hypertension as described above, or during continuous, periodic, or manual activation of the stimulus generator in those embodiments, the programmed pulse signal is generated from the output circuit of stimulus generator 10. The pulse signal is applied to the set of nerve electrodes 30 for stimulating the patient's vagus nerve 28. Patient discomfort may be alleviated by a ramping up the pulses during the first two seconds of stimulation, rather than abrupt application at the programmed level. Additionally, the device may be implemented to permit the patient to interrupt the stimulation by use of the external magnet if the stimulation should produce severe discomfort. The patient would then contact the physician to arrange for reprogramming the output signal level of the device. A conventional clamping circuit (not shown) may be used to limit the maximum voltage (14 volts, for example) deliverable to the vagus nerve, to prevent nerve damage.

Figure 3:
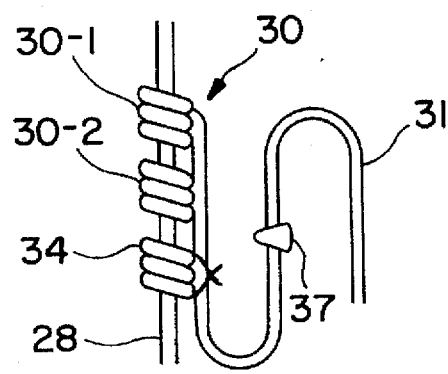
FIG. 3 is a detailed fragmentary illustration of the nerve electrode as implanted on the patient's vagus nerve to modulate the electrical activity of the nerve in response to application of the electrical stimulus.

The stimulating nerve electrode set 30 is shown in greater detail in FIG. 3. The electrode set is conductively connected to the distal end of a pair of insulated electrical conductors in lead 31. Electrode set 30 includes bipolar stimulating electrodes 30-1 and 30-2, preferably of the type described in U.S. Pat. No. 4,573,481 to Bullara (the '481 patent). The electrode assembly is surgically implanted on the patient's vagus nerve 28 at a suitable site, preferably in the patient's neck. Electrodes 30-1 and 30-2 are installed on the nerve, and the electrode set is further retained in place by a spiral anchoring tether 34 such as that disclosed in U.S. Pat. No. 4,979,511 to Reese S. Terry, Jr. and assigned to the same assignee as the instant application. Lead 31 is secured in a manner to allow flexing with patient movement, by means of a suture connection 37 to nearby tissue.

The open helical design of electrode set 30 (described in detail in the '481 patent) is self-sizing and flexible, and thus minimizes trauma to the nerve while allowing body fluid interchange with the nerve. The electrode assembly conforms to the shape of the nerve, providing a low stimulation threshold by allowing a larger stimulation contact area. Structurally, the electrodes are two ribbons of platinum, which may be coated with iridium oxide, individually bonded to the inside surface of respective spiral loops 30-1 and 30-2 of a three-loop helical assembly. The two conductive lead wires are welded to respective ones of these conductive ribbon electrodes. The remaining portion of each loop is silicone rubber, and the third loop 34 is merely the tether. The inner diameter of electrode assembly 30 is approximately two millimeters (mm), and each individual spiral loop is about seven mm long (measured along the axis of the nerve).

Figure 4:
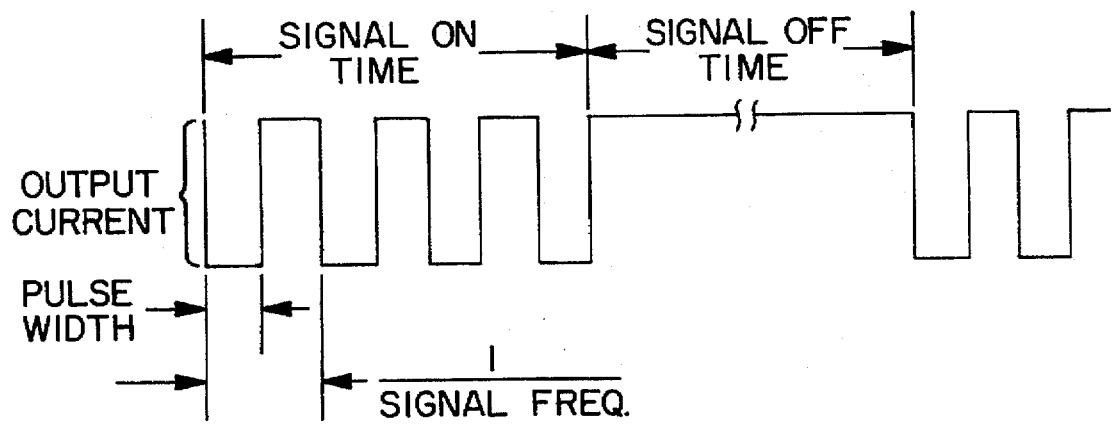
FIG. 4 is an illustrative idealized electrical output signal waveform of the stimulus generator.

FIG. 4 is an idealized representation of the output signal waveform delivered by output circuit 13 of the neurostimulator to electrode set 30. This Figure is especially useful to illustrate the configurable (programmable) parameters on-time, off-time, frequency, pulse width, and output current for the output signal.

For use of the neurostimulator to relieve refractory hypertension, the approximate values of typical stimulating parameters are: pulse frequency of 20 Hertz (Hz), pulse width of one millisecond (ms), and output current of two milliamperes (ma), with a range from 5 to 50 Hz, 0.1 to 3 ms, and 0.1 to 4 ma, respectively. Typical on time is 30 seconds (sec) with a range from 5 sec to 2 minutes. Typical off time is 5 minutes, with a range from 3 minutes to ten minutes. Such stimulation modulates electrical activity of the vagus nerve in a manner tending to reduce mean arterial pressure by sending signals via vagus projections to higher brain nuclei associated with pressure regulation and peripheral vascular resistance.

The vagus nerve may have on the order of approximately 100,000 fibers (axons) of three different sizes classified as A, B and C which carry signals to and from the brain and other parts of the body. A and B fibers have a myelin sheath, while the C fibers are unmyelinated. Myelinated fibers are generally larger, conduct faster with lower stimulation thresholds, and exhibit a particular strength-duration curve in response to a specific width and amplitude of stimulation pulse, as compared to unmyelinated fibers. A and B fibers can be stimulated with relatively narrow pulse widths, from 50 to 200 microseconds (µs), for example. C fibers typically require wider pulse widths (e.g., 300–1000 µs) and higher amplitudes for activation. Thus, A and B fibers can be stimulated without stimulating C fibers.

Electrical stimulation of nerve fibers typically causes neural signals to flow in both directions, but in the vagus nerve each axon exhibits only unidirectional electrical conduction in normal circumstances. According to the scientific literature, the vagus nerve is composed of somatic and visceral afferents (inward conducting nerve fibers that convey impulses toward a nerve center such as the brain or spinal cord) and efferents (outward conducting nerve fibers that convey impulses to an effector to stimulate it and produce activity). Most vagal nerve fibers are of the C type, principally visceral afferents having cell bodies lying in masses or ganglia in the neck. The central projections terminate in the nucleus of the solitary tract which sends fibers to various regions of the brain, including the hypothalamus, thalamus, and amygdala. Others continue to the medial reticular formation of the medulla, the cerebellum, the nucleus cuneatus and other regions.

By appropriately setting pulse width and amplitude of the electrical signal delivered to the vagus nerve, the nerve fibers can be selectively stimulated, such as A and not B and C; or A and B, but not C; or A, B and C.

Various related factors may need to be considered in the programming process, such as use of the knowledge that C fibers conduct signals very slowly to recognize that they will not be highly responsive to attempts at rapid stimulation, and thus that a short pulse train should be used. The fibers would become refractory to stimulation within a relatively short time interval and thus incapable of tracking the pattern of a longer pulse train. After a suitable recovery period, another short pulse train may be applied to achieve further treatment. The precise pattern to be used, e.g., the length of the time intervals on and off, will depend on and be adjusted to the individual patient.

Whether through direct input to the autonomic nervous system via the main trunk of the vagus nerve, or indirectly through innervation of the aortic arch sinus by the vagus nerve, the technique afforded by the present invention provides another therapeutic option for physicians, at least when it has been determined that the patient's refractory hypertension is not adequately responsive to traditional treatment such as drug therapy.

Figure 5:
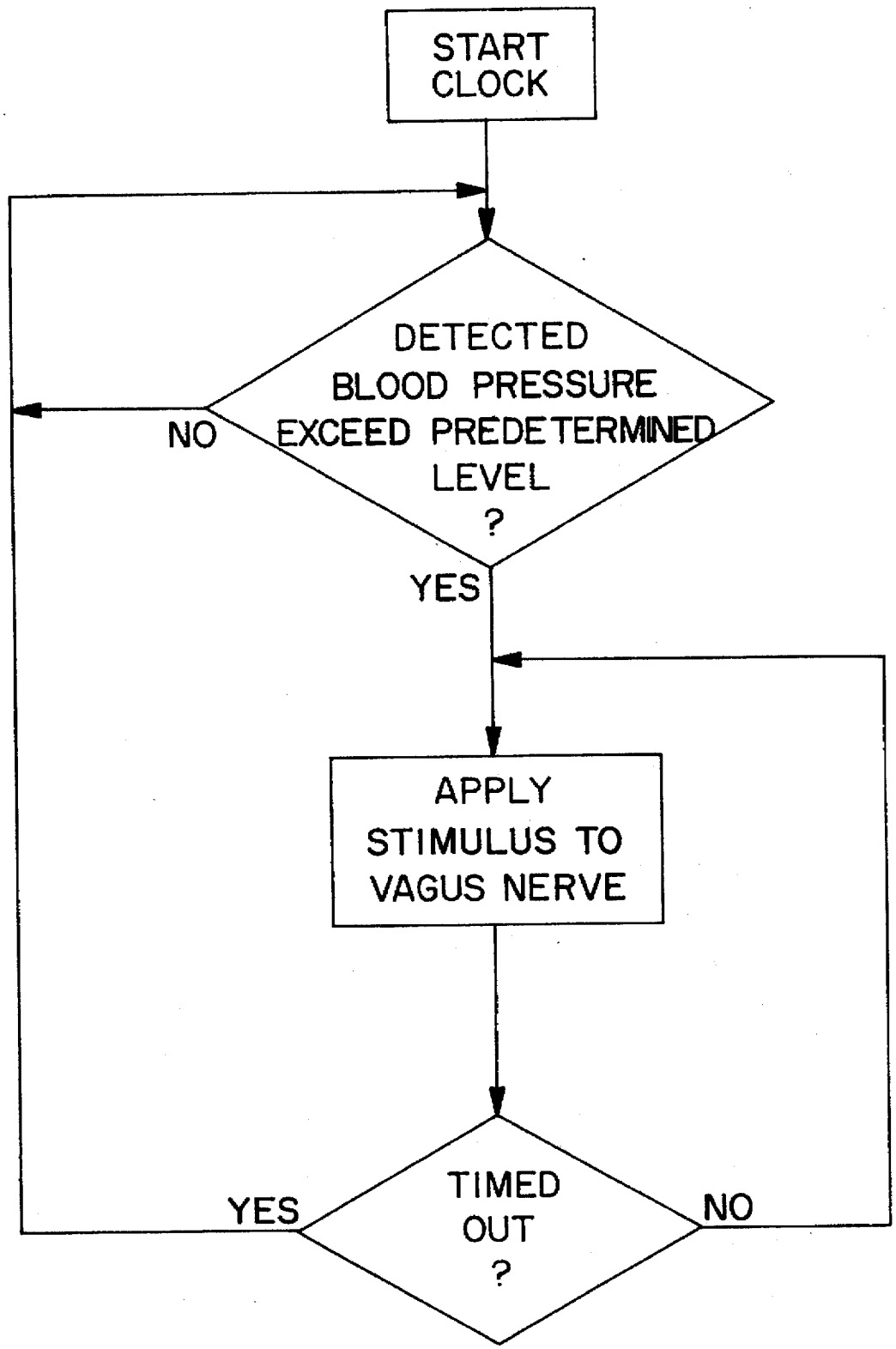
FIG. 5 is a flow chart to illustrate a device-implemented method of treating refractory hypertension.

FIG. 5 is a flow chart illustrating the device-implemented method of treating and controlling the refractory hypertension disorder. In a method of treating a patient suffering from refractory hypertension, the medical therapeutic device of the invention is implanted in the patient's body, and the device itself implements further steps of the method. It continually monitors the blood pressure of the patient (systolic and/or diastolic) to detect elevated blood pressure. Specifically, a pressure which is elevated above a preset threshold level is taken as indicating a need to initiate treatment to alleviate hypertension.

As described above, detection of elevated blood pressure may be accomplished using an electrode array implanted adjacent to an artery proximate the patient's heart, where it will sense the relatively small electrical resistance changes that accompany periodic blood pressure variations of the patient, or using the conventional cuff-type of monitor with electrode and telemetry coil. Detected changes produce lower and higher amplitudes of the signal detected by the electrode array. Logic in the detection circuit determines the patient's systolic and diastolic blood pressure from these amplitude variations, in the form of a digital output signal. This signal is applied to the logic and control circuit, and is monitored to ascertain an elevated level of the patient's systolic and/or diastolic blood pressure that warrants intervention with hypertension therapy. The stimulating electrical signal is then generated in an appropriately configured form, and applied to the electrode assembly implanted on the patient's vagus nerve for a prescribed time period, to reduce the elevated blood pressure and relieve the hypertension.

The electrical stimulus is configured by programming to modulate the electrical activity of the nerve such that the hypertension is alleviated. In particular, the stimulus is configured as a pulsed signal by programming parameters of the signal including on-time, off-time, frequency, pulse width, and current.

If, however, the patient's blood pressure as monitored by the system is not elevated, or if the stimulus (after it has timed out) has resulted in a reduction of the blood pressure below the predetermined threshold, so that the pressure as monitored is no longer elevated, no further stimuli are applied to the vagus nerve. The system remains in its monitoring mode in either event.

Although certain preferred embodiments and methods have been described herein, it will be apparent to those skilled in the art from the foregoing description that variations and modifications of the preferred embodiments, methods and techniques may be made without departing from the true spirit and scope of the invention. For example, the stimulus generator may be external to the patient's body, with only an RF coil, rectifier and the lead/nerve electrode assembly implanted; or with the lead implanted percutaneously through the skin and to the nerve electrode. Although special precautions are necessary to prevent infection, this procedure allows a relatively simple determination of whether the hypertension is successfully treated by this method. If it is, a permanent implant may be provided. Disadvantages of a partially implanted device include the inconvenience of carrying the external transmitter on the patient's person, and the need for greater power for activation than if the system were totally implanted.

Accordingly, it is intended that the invention shall be limited only to the extent required by the appended claims and the rules and principles of applicable law.

What is claimed is:

1. A method of treating patients suffering from refractory hypertension, comprising the steps of:

implanting a neurostimulating device constructed and arranged to generate a stimulating electrical signal as an output thereof in the body of the patient operative to sense a prescribed event indicative of an imminent need for treatment of the refractory hypertension, said prescribed event being the patient's blood pressure exceeding a programmed threshold level, the step of implanting including connecting said output directly to the vagus nerve of the patient for application of said stimulating electrical signal thereto, and programming the device to automatically respond to the sensed occurrence of the prescribed event with application of a stimulating electrical signal having programmed electrical parameters to the patient's vagus nerve to modulate the electrical activity of the vagus nerve in a manner to alleviate the refractory hypertension.

2. The method of claim 1, further including:

providing a capability for manual activation of the device by the patient upon sensing symptoms of refractory hypertension.

3. The method of claim 1, further including:

programming the device to produce a periodic stimulating electrical signal to modulate electrical activity of the vagus nerve according to the patient's circadian rhythm.

4. The method of claim 1, wherein:

the predetermined stimulating electrical signal is a pulse waveform with signal parameters programmed to modulate electrical activity of the vagus nerve.

5. The method of claim 4, including:

programming parameter values of the pulse waveform, including pulse width, output current, frequency, on time and off time before application of the stimulating electrical signal to the vagus nerve.

6. The method of claim 1, including:

applying said stimulating signal to the patient's vagus nerve by connecting said output of the device to a nerve electrode implanted on the vagus nerve at a site in the patient's neck.

7. A method of treating a patient suffering from refractory hypertension in which a medical therapeutic device is implanted in the patient's body, comprising the device-implemented steps of:

detecting elevated blood pressure of the patient as indicating a need to initiate treatment to alleviate the hypertension, and after detecting the elevated blood pressure, applying an electrical stimulus directly to the patient's vagus nerve, said stimulus being configured to modulate the electrical activity of the nerve such that the hypertension is alleviated.

8. The method of claim 7, wherein the detecting step is performed by sensing blood pressure by means of a pressure detector wrapped on the upper arm of the patient.

9. The method of claim 7, wherein the detecting step is performed by sensing electrical impedance changes with undulations of blood pressure at a site adjacent an artery of the patient.

10. The method of claim 7, wherein the electrical stimulus is configured as a pulsed signal by programming parameters of the signal including on-time, off-time, frequency, pulse width, and current.

* * * * *